(12) United States Patent
Buree

(10) Patent No.: US 7,709,752 B2
(45) Date of Patent: May 4, 2010

(54) LASER SURGERY STATION POWER SYSTEM

(75) Inventor: John Buree, Goleta, CA (US)

(73) Assignee: Electri-City, Inc., Goleta, CA (US)

( * ) Notice: Subject to any disclaimer, the term of this patent is extended or adjusted under 35 U.S.C. 154(b) by 562 days.

(21) Appl. No.: 11/690,771

(22) Filed: Mar. 23, 2007

(65) Prior Publication Data
US 2008/0289872 A1  Nov. 27, 2008

(51) Int. Cl.
| H05K 5/00 | (2006.01) |
| H01R 13/46 | (2006.01) |
| A47B 71/00 | (2006.01) |

(52) U.S. Cl. ............... 174/520; 174/60; 5/600
(58) Field of Classification Search ........... 174/520, 174/559, 60, 63, 64; 5/600
See application file for complete search history.

(56) References Cited

U.S. PATENT DOCUMENTS

| 5,735,278 A * | 4/1998 | Hoult et al. ............... 600/422 |
| 5,795,351 A * | 8/1998 | Clapham ........................ 606/4 |
| 6,170,102 B1 * | 1/2001 | Kreuzer ........................ 5/601 |
| 6,246,200 B1 * | 6/2001 | Blumenkranz et al. .. 318/568.11 |
| 6,349,436 B1 * | 2/2002 | Kreuzer ........................ 5/600 |
| 7,073,222 B1 * | 7/2006 | Skripps ........................ 5/618 |
| 7,109,416 B1 * | 9/2006 | Reed ............................ 174/50 |
| 7,254,850 B2 * | 8/2007 | Newkirk et al. ................ 5/600 |
| 7,385,137 B2 * | 6/2008 | Burke et al. .................. 174/50 |
| 2004/0164220 A1 * | 8/2004 | Newkirk ..................... 248/647 |
| 2004/0199996 A1 * | 10/2004 | Newkirk et al. ............ 5/81.1 R |

\* cited by examiner

Primary Examiner—Hung V Ngo
(74) Attorney, Agent, or Firm—Felix L. Fischer

(57) ABSTRACT

A surgery power station incorporates a pedestal having at least one internal power panel and a conduit extending from the pedestal and communicating with the interior of the pedestal through a first aperture. The conduit extends upward for engagement to an electrical box integral with a ceiling structure of an operating theater. A channel extends through the conduit and is connected to a central support structure within the pedestal providing a race for primary electrical cabling routed through the ceiling structure from a remote UPS to the operating theater. A primary electrical panel is mounted to the central support structure and connected to the primary electrical cabling. The primary electrical panel provides operating power electrical connectors for an operating theater system such as an opthamological surgery laser. A reagent gas line extends through the conduit and terminates in a connector on the pedestal for connection to the operating theater system.

5 Claims, 5 Drawing Sheets

LASER SURGERY STATION POWER SYSTEM

BACKGROUND OF THE INVENTION

1. Field of the Invention

This invention relates generally to the field of uninterruptible power systems and, more particularly, to an access panel system for remote connection of laser surgery systems to a UPS and other utility systems thereby allowing the operating theater to remain quiet and uncluttered without presence of the UPS.

2. Description of the Related Art

Surgical operating theaters require uninterruptible power capability for all systems involved in surgery to protect surgery patients. This is particularly true of laser surgery systems such as those employed in ophthamological surgery. In current practice, commercial uninterruptible power supplies (UPS) are provided in the operating theaters to assure that power is available for the laser system independent of grid power interruptions. UPS devices for high power operation are typically quite large and may emit noise, heal or other emissions not conducive to the operating theater environment.

Additionally, laser systems typically require reagent gases for operation of the laser. Currently such reagent gasses are stored either in pressure containers in the operating theater or in containers remotely located with separate plumbing systems routed to the operating theater for access by the laser.

Telecommunications lines are also employed regularly in modern operating theaters for normal voice phone service as well as computer network connection. In many laser systems, computer control is employed and connection to network capability for these computers allows rapid update and in certain instances remote operation or control of the operating systems.

It is therefore desirable that electrical attachment for a surgical laser be provided through a convenient source or pedestal without the presence of the UPS in the operating theater. It is further desirable that reagent gas supplies be provided remotely with source connectors in the same pedestal as the electrical connections for the laser. It is also desirable that the centralized pedestal be provided with easy access for connection of both electrical and reagent gas systems including additional incidental electrical attachment for operating theater tools or systems. Connections for telecommunications within the same pedestal also provides ease of access.

SUMMARY OF THE INVENTION

The present invention provides a surgery power station that incorporates a pedestal having at least one internal power panel and a conduit extending from the pedestal, and communicating with the interior of the pedestal through a first aperture. The conduit extends upward for engagement to an electrical box integral with a ceiling structure of an operating theater. A channel extends through the conduit and is connected to a central support structure within the pedestal providing a race for primary electrical cabling routed through the ceiling structure from a remote UPS to the operating theater. A primary electrical panel is mounted to the central support structure and connected to the primary electrical cabling. The primary electrical panel is accessible through a first entry door in the pedestal and provides operating power electrical connectors for power cord engagement to an operating theater system such as an opthamological surgery laser. At least one second aperture is provided for routing of the power cord from the operating theater system. A reagent gas line extends through the conduit and terminates in a connector on the pedestal for connection to the operating theater system.

BRIEF DESCRIPTION OF THE DRAWINGS

These and other features and advantages of the present invention will be better understood by reference to the following detailed description when considered in connection with the accompanying drawings wherein.

DETAILED DESCRIPTION OF THE INVENTION

Figure 1:
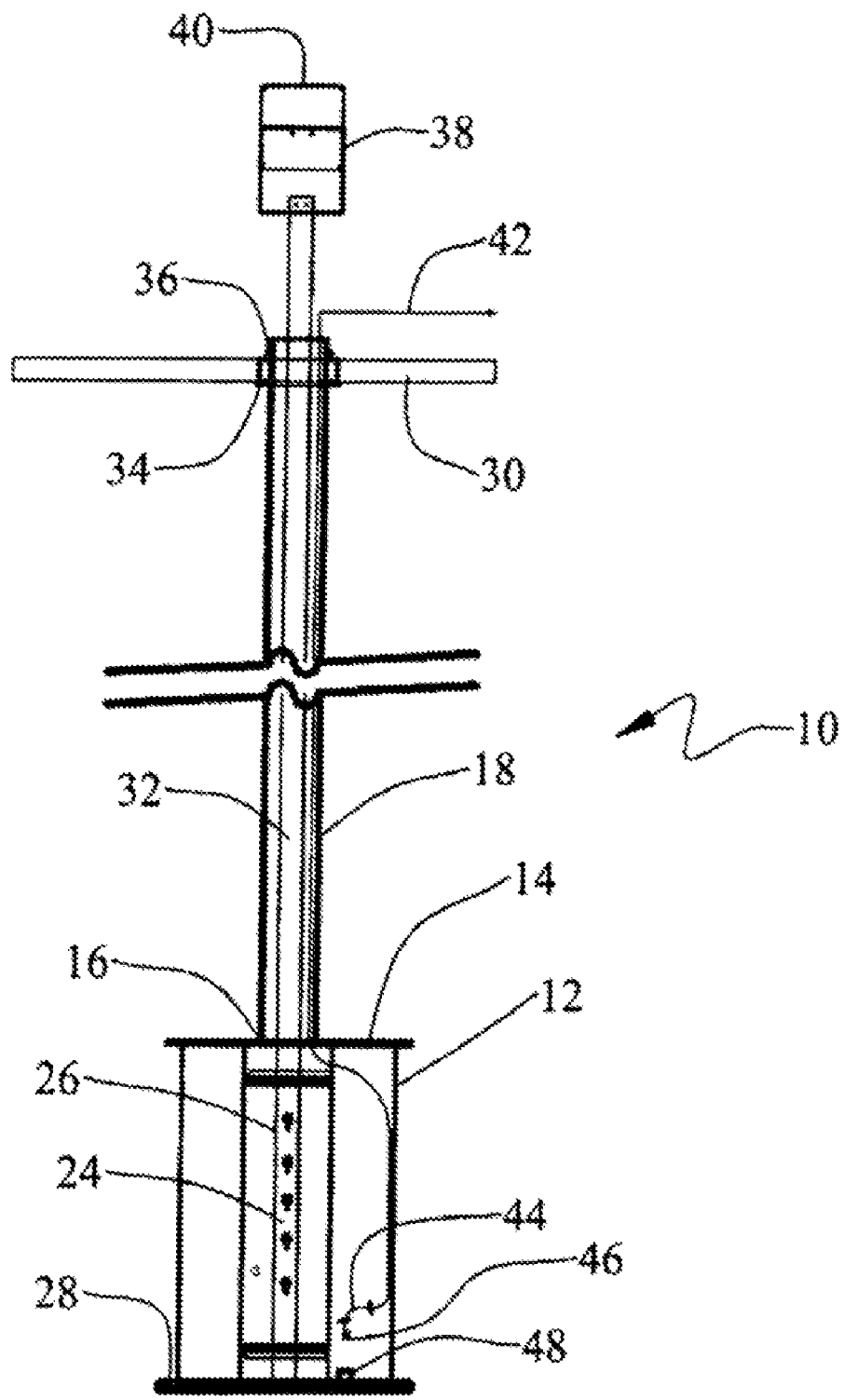
FIG. 1 is a front view of a laser surgery power station according to the present invention.

Referring to the drawings, FIG. 1 shows a laser surgery power station 10 which incorporates a multilateral pedestal 12. A top plate top 14 closes the upper end of the pedestal and an aperture 16 in the tale top allows communication for a conduit 18 with the internal volume of the pedestal. For the embodiment shown in the drawings, the pedestal is hexagonal for reduced footprint and employs two doors 20, 22 (best seen in FIGS. 3 and 4) in two opposite sides of the hexagon. The front view shown in FIG. 1 with door 20 removed for clarity shows the primary internal power strip 24 which is incorporated on a central frame structure 26 extending from the top plate to an interface 28 between the pedestal and the floor of the operating theater. The primary power strip provides connection outlets for primary power to the laser. For the embodiment shown, the primary power is 208 volt three phase, as will be described in greater detail subsequently. Multiple outlets are provided and may be selectively segregated between house power and UPS power depending on the required application.

Conduit 18 extends from the top plate top of the pedestal upward to a height required for entry into a suspended ceiling 30 in the operating theater. For typical installations, the ceiling will be a standard acoustical panel arrangement. In alternative embodiments, enclosed wiring conduits or raceways are engaged with the conduit for wiring runs. Contained within the conduit is a channel 32 which is integral with or structurally engaged to the central frame structure. For the embodiment shown in the drawings, a trim plate 34 finishes the hole in the suspended ceiling and is secured to the conduit with suspension springs 36. The channel extends from the conduit to engage a J-box 38 mounted within the ceiling structure of the operating theater. A seismic support plate 40 is rigidly attached to the channel web and provides closure for the J-box. The flanges of the channel extending from the web provide a race for wire bundles as will be described in with respect to FIGS. 4 and 5.

For the embodiment shown in the drawings, a reagent gas line 42 is routed through the ceiling structure of the operating theater and descends through the conduit into the pedestal. In the exemplary embodiment shown, a flexwhip 44 is employed at the terminal end of the gas line for stress relief. A Swagelock® bulkhead coupling 46 or comparable connector is mounted in the pedestal wall for internal connection of the flexwhip and provides a connection external to the pedestal for a feed line to the laser system. For the particular embodiment shown, an access arch 48 is provided for routing of electrical cabling from the laser for power connection to the primary internal power strip. Opening of the doors in the pedestal allows easy access to the power strip and feeding of power cable plugs through the access arch. The embodiment shown provides for internal connection of power cords to the internal power strip to avoid disturbance of the power cords or inadvertent disconnection.

Figure 2:
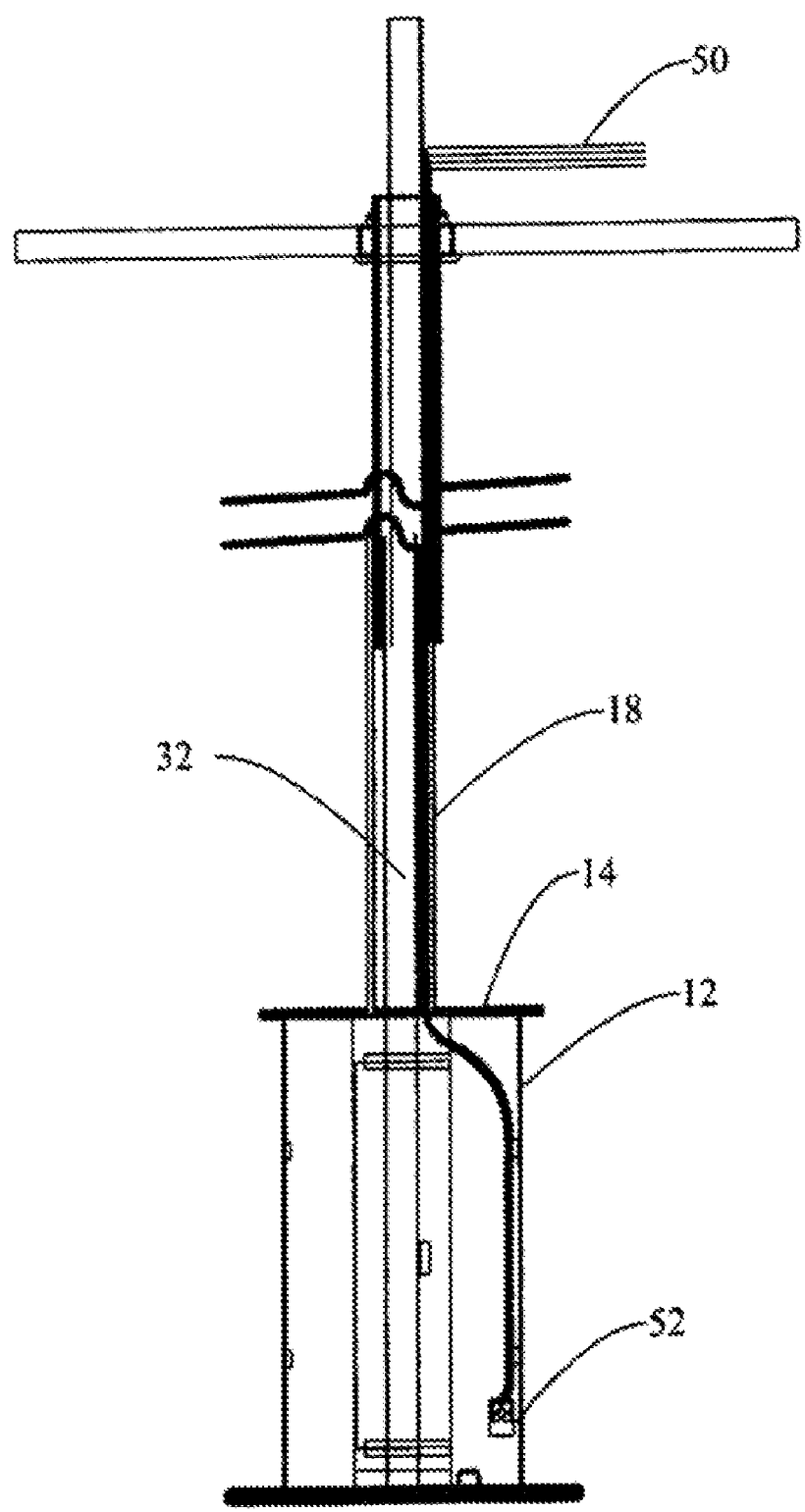
FIG. 2 is a rear view of the laser surgery power station.

As seen in FIG. 2, telecommunications cables 50 are routed through the conduit from races in the ceiling structure of the operating theater to the pedestal. A connector jack 52 in the wall of the pedestal provides for internal connection of the cables and external connection of telephone and computer network adapters and cords. The structure provided by mounting the channel central to the conduit provides separation of the cable runs from the gas line and electrical wire bundles.

Figure 3:
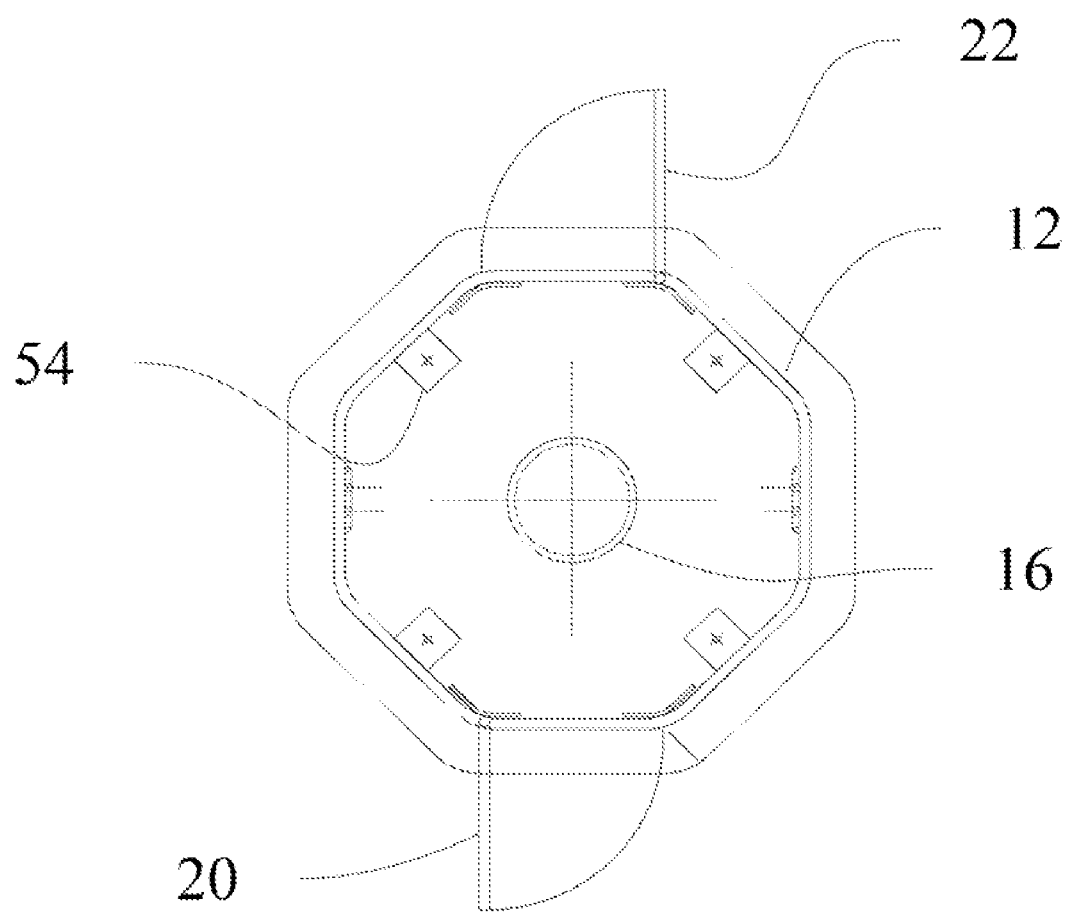
FIG. 3 is a top view of the laser surgery power station with the pedestal top plate and center structure shown in phantom for clarity of the wall and conduit features.

The hexagonal shape of the pedestal for the exemplary embodiment is shown in FIG. 3. For this embodiment, doors 20 and 22 are located in opposing side panels in pedestal 12. The side panels of the pedestal are interchangeable and allow arrangement of the doors as desired for desired access. Angle brackets 54 are attached to selected sides of the pedestal for secure mounting of the pedestal to the floor.

Figure 4:
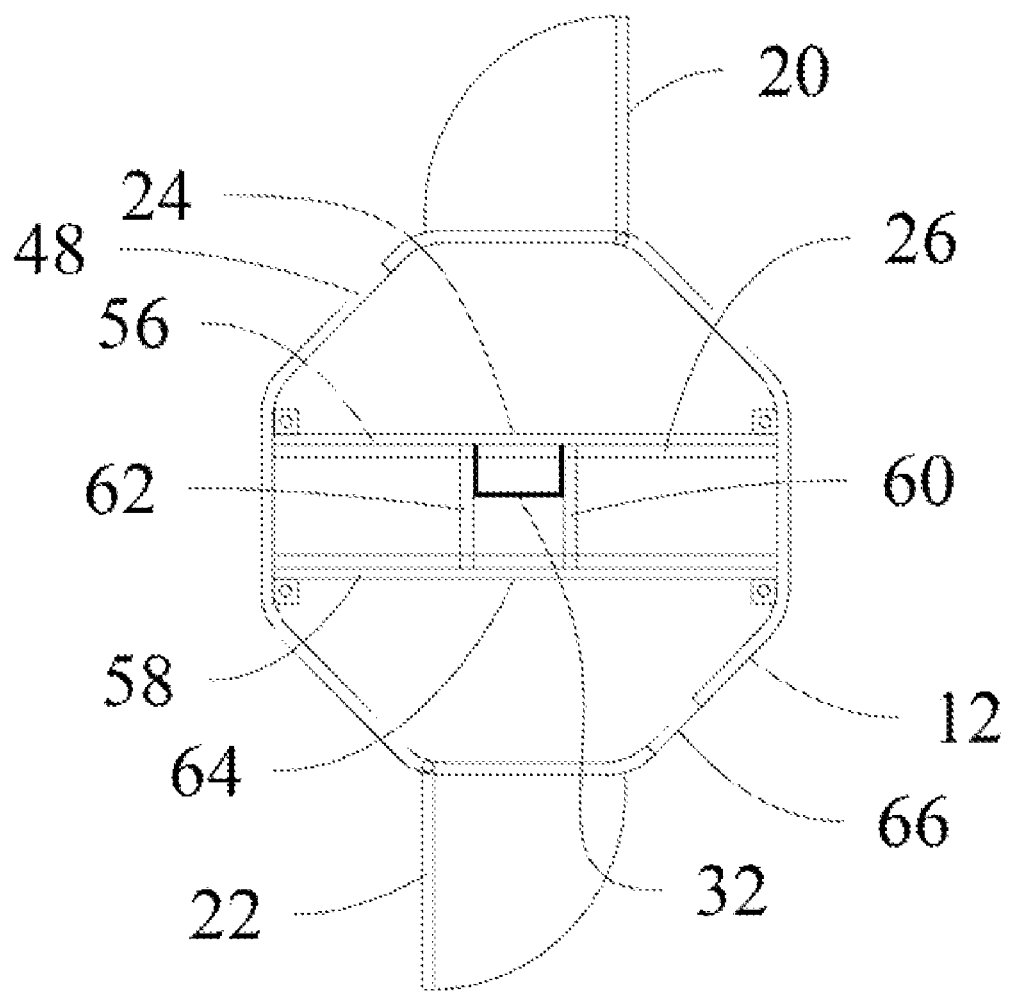
FIG. 4 is a bottom view of the laser surgery power station showing the center structure; and, FIG. 5 is a schematic diagram of remote UPS connection to the laser surgery power station.

Viewing the pedestal from the bottom, in FIG. 4, central frame structure 26 for the exemplary embodiment is shown in detail. Side plates 56, 58 extend between opposing walls of the hexagonal pedestal, separated by web plates 60, 62 which create an internal conduit for electrical cabling. Channel 32 extends from conduit 18 into this internal conduit. For the embodiment shown, the channel is closely received by the web plates to bifurcate the internal conduit into two separate elements, one of which carries cables for the primary 208V power and the other which is employed for standard 110V AC power. In alternative embodiments, an additional channel is mounted back to back in opposing relationship to the first channel to create additional raceways for cable runs. In such larger units, up to 10 primary power circuits connectors for operating theater system operation are provided on the primary panel. As seen in FIG. 2, standard duplex outlets ate provided in secondary power panel 64 accessed through door 22. A second access arch 66 is provided for routing AC power cables into the pedestal for connection to the secondary power panel.

Figure 5:
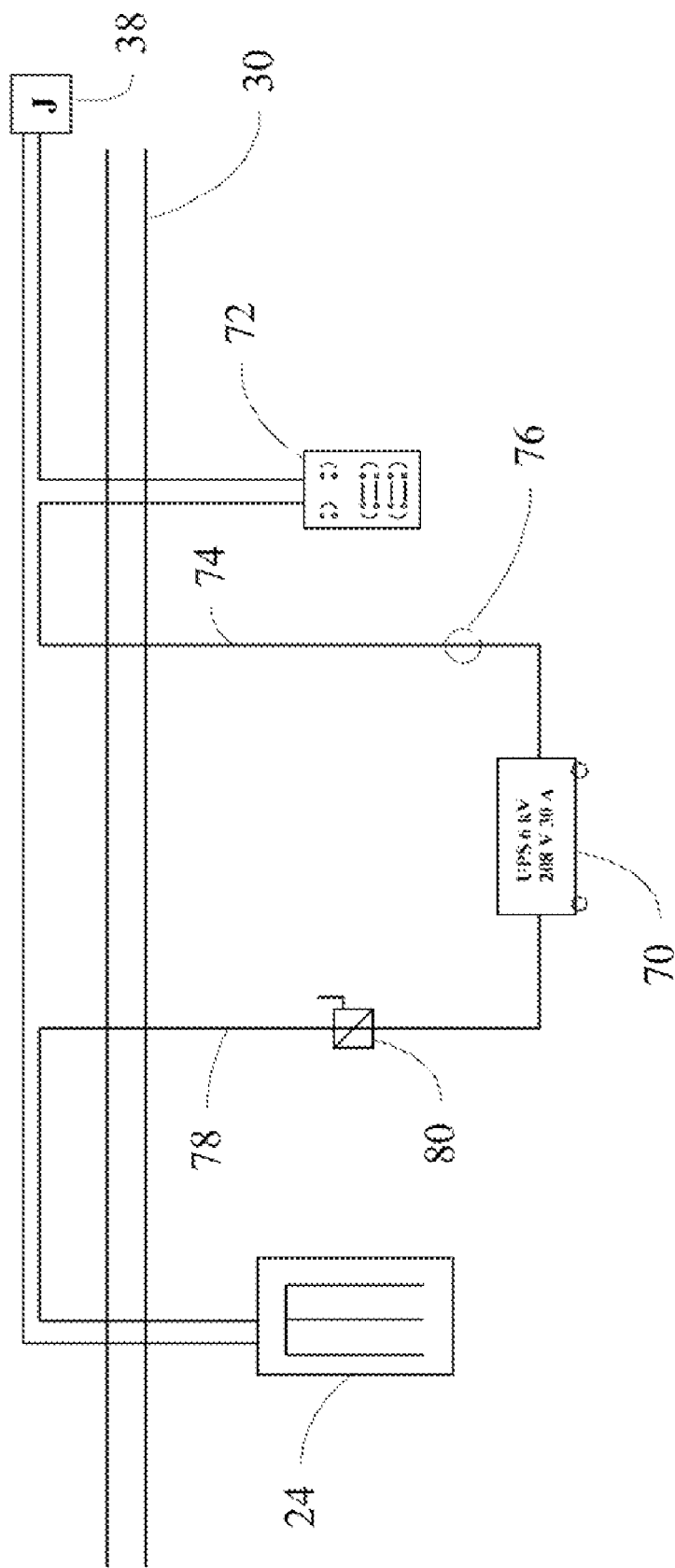

FIG. 5 schematically demonstrates an exemplary electrical connection for a UPS and house power system to the laser surgery power station. A UPS 70, such as a 6 kV 208V 30 A supply provided by vendors such as Allegreto or VSX, is mounted in a room remote from the operating theater. House power is provided through a breaker panel 72 having 208V power and standard 110V AC. Cabling run 74 provides power from the breaker panel to the UPS via a 1" conduit and employs a circuit breaker 76 for additional circuit protection. The UPS provides power to the primary panel in the surgical power station through cable run 78 via a 1" conduit and employs a fused disconnect 80 for standard mounting and connection of the UPS. Cable run 78 extends through the suspended ceiling for routing through conduit 18 into the pedestal for connection to the primary power panel. House power is routed directly to the primary panel from the breaker panel through J-box 38 in the suspended ceiling and through conduit 18 using channel 32 as a race to primary panel 24 in the pedestal for the exemplary embodiment. 110V AC circuits are fed through comparable cable runs in the suspended ceiling, through conduit 18 and to secondary panel 64.

Having now described the invention in detail as required by the patent statutes, those skilled in the art will recognize modifications and substitutions to the specific embodiments disclosed herein. Such modifications are within the scope and intent of the present invention as defined in the following claims.

What is claimed is:

1. A surgery power station comprising:
   a pedestal having at least one internal power panel;
   a conduit extending from the pedestal and communicating with the interior of the pedestal through a first aperture, the conduit extending for engagement to an electrical box integral with a ceiling structure of an operating theater;
   a channel extending through the conduit and connected to a central support, structure within the pedestal, the channel providing a race for primary electrical cabling routed through the ceiling structure from a remote UPS to the operating theater;
   a primary electrical panel mounted to the central support structure and connected to the primary electrical cabling, the primary electrical panel accessible through a first entry door in the pedestal and providing operating power electrical connectors for power cord engagement to an operating theater system;
   at least one second aperture for routing of the power cord from the operating theater system; and,
   a reagent gas line extending through the conduit and terminating in a connector on the pedestal for connection to the operating theater system.

2. A surgery power station as defined in claim 1 wherein the operating theater system is a laser.

3. A surgery power station as defined in claim 1 further comprising a secondary electrical panel providing standard alternating current electrical connectors for power cord engagement to standard AC devices, the secondary electrical panel mounted to the central support structure and connected to secondary electrical cabling routed through the conduit.

4. A surgery power station as defined in claim 3 further comprising a third aperture in the pedestal for routing of the AC power cord.

5. A surgery power station as defined in claim 1 further comprising a telecommunications interface on the pedestal for attachment of voice telephone and data network devices and telecommunications cables routed from the telecommunications interface through the conduit for remote connection.

\* \* \* \* \*